United States Patent
Séguin et al.

(10) Patent No.: US 8,864,817 B2
(45) Date of Patent: *Oct. 21, 2014

(54) ENDOPROSTHESIS FOR VASCULAR BIFURCATION

(76) Inventors: Jacques Séguin, Windsor (GB); Jean-Claude LaBorde, Vieille-Toulouse (FR)

(*) Notice: Subject to any disclaimer, the term of this patent is extended or adjusted under 35 U.S.C. 154(b) by 0 days.

This patent is subject to a terminal disclaimer.

(21) Appl. No.: 13/544,714

(22) Filed: Jul. 9, 2012

(65) Prior Publication Data

US 2013/0041450 A1    Feb. 14, 2013

Related U.S. Application Data

(63) Continuation of application No. 11/124,905, filed on May 9, 2005, now Pat. No. 8,231,667, which is a continuation of application No. PCT/EP02/12509, filed on Nov. 8, 2002.

(51) Int. Cl.
| | | |
|---|---|---|
| *A61F 2/86* | (2013.01) | |
| *A61F 2/90* | (2013.01) | |
| *A61F 2/91* | (2013.01) | |
| *A61F 2/915* | (2013.01) | |
| *A61F 2/95* | (2013.01) | |
| *A61F 2/06* | (2013.01) | |
| *A61F 2/954* | (2013.01) | |

(52) U.S. Cl.
CPC ... *A61F 2/91* (2013.01); *A61F 2/90* (2013.01); *A61F 2/915* (2013.01); *A61F 2002/91541* (2013.01); *A61F 2250/0039* (2013.01); *A61F 2/95* (2013.01); *A61F 2002/91558* (2013.01); *A61F 2002/067* (2013.01); *A61F 2/954* (2013.01)
USPC ........................................................ 623/1.15

(58) Field of Classification Search
USPC ................................ 623/1.15, 1.3, 1.31, 1.35
See application file for complete search history.

(56) References Cited

U.S. PATENT DOCUMENTS

| | | |
|---|---|---|
| 3,657,744 A | 4/1972 | Ersek |
| 3,805,301 A | 4/1974 | Liebig |

(Continued)

FOREIGN PATENT DOCUMENTS

| | | |
|---|---|---|
| EP | 0 335 341 B1 | 3/1992 |
| EP | 0 520 721 A2 | 6/1992 |

(Continued)

OTHER PUBLICATIONS

Abizaid et al., "One-Year Follow-up After Intravascular Ultrasound Assessment of Moderate Left Main Coronary Artery Disease in Patients with Ambiguous Angiograms", *JACC* vol. 34, No. 3 , pp. 707-715 (1999).

(Continued)

*Primary Examiner* — Ryan Severson
(74) *Attorney, Agent, or Firm* — Kilpatrick Townsend & Stockton LLP

(57) ABSTRACT

An apparatus for treating an area of bifurcation where a principal body conduit separates into at least two secondary conduits comprises a radially expandable first stent body. The first stent body has a substantially conical shape and a first end having a greater diameter than a second end when fully expanded. The first stent body is preferably shaped to be independent of any other stent bodies, and is free of any means for connecting to any other stent bodies when fully expanded.

17 Claims, 3 Drawing Sheets

(56) References Cited

U.S. PATENT DOCUMENTS

| | | |
|---|---|---|
| 3,818,511 A | 6/1974 | Goldberg et al. |
| 3,945,052 A | 3/1976 | Liebig |
| 4,390,599 A | 6/1983 | Broyles |
| 4,562,596 A | 1/1986 | Kornberg |
| 4,733,065 A | 3/1988 | Hoshi et al. |
| 4,733,665 A | 3/1988 | Palmaz |
| 4,768,507 A | 9/1988 | Fischell et al. |
| 4,800,882 A | 1/1989 | Gianturco |
| 4,886,062 A | 12/1989 | Wiktor |
| 4,994,071 A | 2/1991 | MacGregor |
| 5,019,090 A | 5/1991 | Pinchuk et al. |
| 5,045,072 A | 9/1991 | Castillo et al. |
| 5,064,435 A | 11/1991 | Porter |
| 5,102,417 A | 4/1992 | Palmaz |
| 5,104,404 A | 4/1992 | Wolff |
| 5,135,536 A | 8/1992 | Hillstead |
| 5,192,297 A | 3/1993 | Hull |
| 5,195,984 A | 3/1993 | Schatz |
| 5,197,978 A | 3/1993 | Hess |
| 5,211,658 A | 5/1993 | Clouse et al. |
| 5,211,663 A | 5/1993 | Kovacs et al. |
| 5,219,355 A | 6/1993 | Parodi et al. |
| 5,234,457 A | 8/1993 | Andersen |
| 5,269,802 A * | 12/1993 | Garber .................. 623/1.15 |
| 5,282,824 A | 2/1994 | Gianturco |
| 5,316,023 A * | 5/1994 | Palmaz et al. ............ 128/898 |
| 5,330,500 A | 7/1994 | Song |
| 5,356,423 A | 10/1994 | Tihon et al. |
| 5,360,401 A | 11/1994 | Turnland |
| 5,360,443 A | 11/1994 | Barone et al. |
| 5,370,683 A | 12/1994 | Fontaine |
| 5,387,235 A | 2/1995 | Chuter |
| 5,405,378 A | 4/1995 | Strecker |
| 5,443,498 A | 8/1995 | Fontaine |
| 5,445,646 A | 8/1995 | Euteneuer et al. |
| 5,456,713 A | 10/1995 | Chuter |
| 5,466,242 A | 11/1995 | Mori |
| 5,499,973 A | 3/1996 | Saab |
| 5,510,077 A | 4/1996 | Dinh et al. |
| 5,514,154 A | 5/1996 | Lau et al. |
| 5,514,178 A | 5/1996 | Torchio |
| 5,540,701 A | 7/1996 | Sharkey et al. |
| 5,562,697 A | 10/1996 | Christiansen |
| 5,562,724 A | 10/1996 | Vorwerk et al. |
| 5,562,726 A | 10/1996 | Chuter |
| 5,571,135 A | 11/1996 | Fraser |
| 5,571,168 A | 11/1996 | Toro |
| 5,571,170 A | 11/1996 | Palmaz et al. |
| 5,571,173 A | 11/1996 | Parodi |
| 5,591,228 A | 1/1997 | Edoga |
| 5,603,721 A | 2/1997 | Lau et al. |
| 5,609,605 A | 3/1997 | Marshall et al. |
| 5,609,627 A | 3/1997 | Goicoechea et al. |
| 5,617,878 A | 4/1997 | Taheri |
| 5,628,788 A | 5/1997 | Pinchuk |
| 5,632,762 A | 5/1997 | Myler |
| 5,632,763 A | 5/1997 | Glastra |
| 5,632,771 A | 5/1997 | Boatman et al. |
| 5,632,772 A | 5/1997 | Alcime et al. |
| 5,639,278 A | 6/1997 | Dereume et al. |
| 5,667,486 A | 9/1997 | Mikulich et al. |
| 5,669,880 A | 9/1997 | Solar |
| 5,669,924 A | 9/1997 | Shaknovich |
| 5,676,696 A | 10/1997 | Marcade et al. |
| 5,683,449 A | 11/1997 | Marcade |
| 5,683,451 A | 11/1997 | Lenker |
| 5,693,084 A | 12/1997 | Chuter |
| 5,695,499 A | 12/1997 | Helgerson et al. |
| 5,707,376 A | 1/1998 | Kavteladze et al. |
| 5,709,713 A * | 1/1998 | Evans et al. ............. 623/1.53 |
| 5,716,393 A | 2/1998 | Lindenberg et al. |
| 5,720,735 A | 2/1998 | Dorros |
| 5,720,776 A | 2/1998 | Chuter et al. |
| 5,735,893 A | 4/1998 | Lau et al. |
| 5,741,327 A | 4/1998 | Frantzen |
| 5,749,825 A | 5/1998 | Fischell et al. |
| 5,749,890 A | 5/1998 | Shaknovich |
| 5,755,769 A | 5/1998 | Richard et al. |
| 5,755,771 A | 5/1998 | Penn et al. |
| 5,772,669 A | 6/1998 | Vrba |
| 5,776,142 A | 7/1998 | Gunderson |
| 5,776,184 A | 7/1998 | Tuch |
| 5,788,707 A | 8/1998 | Del Toro et al. |
| 5,797,951 A | 8/1998 | Mueller |
| 5,797,952 A | 8/1998 | Klein |
| 5,800,514 A | 9/1998 | Nunez et al. |
| 5,800,520 A | 9/1998 | Fogarty et al. |
| 5,820,542 A | 10/1998 | Dobakk, III et al. |
| 5,824,040 A | 10/1998 | Cox et al. |
| 5,824,042 A | 10/1998 | Lombardi et al. |
| 5,824,071 A | 10/1998 | Nelson et al. |
| 5,827,321 A | 10/1998 | Roubin et al. |
| 5,833,694 A | 11/1998 | Poncet |
| 5,849,037 A | 12/1998 | Frid |
| 5,851,217 A | 12/1998 | Wolff et al. |
| 5,851,228 A | 12/1998 | Pinheiro |
| 5,851,231 A | 12/1998 | Wolff et al. |
| 5,873,904 A | 2/1999 | Ragheb et al. |
| 5,891,114 A | 4/1999 | Chien et al. |
| 5,893,887 A | 4/1999 | Jayaraman |
| 5,897,588 A | 4/1999 | Hull et al. |
| 5,904,713 A | 5/1999 | Leschinsky |
| 5,910,129 A | 6/1999 | Koblish et al. |
| 5,922,019 A | 7/1999 | Hankh et al. |
| 5,938,697 A | 8/1999 | Killion et al. |
| 5,957,930 A | 9/1999 | Vrba |
| 5,957,949 A | 9/1999 | Leonhardt |
| 5,961,548 A | 10/1999 | Shmulewitz |
| 5,976,155 A | 11/1999 | Foreman et al. |
| 5,980,484 A | 11/1999 | Ressemann et al. |
| 5,980,533 A | 11/1999 | Holman |
| 5,984,955 A | 11/1999 | Wisselink |
| 5,989,280 A | 11/1999 | Euteneuer et al. |
| 5,993,481 A | 11/1999 | Marcade et al. |
| 6,010,530 A | 1/2000 | Goicoechea |
| 6,019,778 A | 2/2000 | Wilson et al. |
| 6,030,415 A | 2/2000 | Chuter |
| 6,042,588 A | 3/2000 | Munsinger et al. |
| 6,042,606 A | 3/2000 | Frantzen |
| 6,053,941 A | 4/2000 | Lindenberg et al. |
| 6,056,776 A | 5/2000 | Lau et al. |
| 6,059,813 A | 5/2000 | Vrba et al. |
| 6,063,113 A | 5/2000 | Kavteladze et al. |
| 6,066,167 A | 5/2000 | Lau et al. |
| 6,068,655 A | 5/2000 | Séguin et al. |
| 6,077,296 A | 6/2000 | Shokoohi et al. |
| 6,093,203 A | 7/2000 | Uflacker |
| 6,096,071 A | 8/2000 | Yadav |
| 6,106,548 A | 8/2000 | Roubin et al. |
| 6,117,140 A | 9/2000 | Munsinger |
| 6,120,522 A | 9/2000 | Vrba et al. |
| 6,120,534 A * | 9/2000 | Ruiz ..................... 623/1.19 |
| 6,129,738 A | 10/2000 | Lashinski et al. |
| 6,143,002 A | 11/2000 | Vietmeier |
| 6,143,016 A | 11/2000 | Bleam et al. |
| 6,146,415 A | 11/2000 | Fitz |
| 6,159,238 A | 12/2000 | Killion et al. |
| 6,159,239 A | 12/2000 | Greenhalgh |
| 6,165,195 A | 12/2000 | Wilson et al. |
| 6,179,858 B1 | 1/2001 | Squire et al. |
| 6,183,509 B1 | 2/2001 | Dibie |
| 6,197,049 B1 | 3/2001 | Shaolian et al. |
| 6,203,568 B1 | 3/2001 | Lombardi |
| 6,210,429 B1 | 4/2001 | Vardi et al. |
| 6,210,431 B1 | 4/2001 | Power |
| 6,221,090 B1 | 4/2001 | Wilson |
| 6,221,098 B1 | 4/2001 | Wilson et al. |
| 6,228,110 B1 | 5/2001 | Munsinger |
| 6,231,598 B1 | 5/2001 | Berry et al. |
| 6,245,100 B1 | 6/2001 | Davila et al. |
| 6,254,633 B1 * | 7/2001 | Pinchuk et al. ............. 623/1.3 |
| 6,258,116 B1 | 7/2001 | Hojeibane |
| 6,258,121 B1 | 7/2001 | Yang et al. |
| 6,261,316 B1 | 7/2001 | Shaolian et al. |

(56) References Cited

U.S. PATENT DOCUMENTS

| | | |
|---|---|---|
| 6,264,682 B1 | 7/2001 | Wilson et al. |
| 6,264,686 B1 * | 7/2001 | Rieu et al. .................... 623/1.16 |
| 6,283,992 B1 | 9/2001 | Hankh et al. |
| 6,293,966 B1 | 9/2001 | Frantzen |
| 6,302,893 B1 | 10/2001 | Limon et al. |
| 6,305,436 B1 | 10/2001 | Andersen et al. |
| 6,309,412 B1 | 10/2001 | Lau et al. |
| 6,315,794 B1 | 11/2001 | Richter |
| 6,322,847 B1 | 11/2001 | Zhong et al. |
| 6,325,819 B1 | 12/2001 | Pavcnik et al. |
| 6,325,820 B1 | 12/2001 | Khosravi et al. |
| 6,325,825 B1 * | 12/2001 | Kula et al. ...................... 623/1.3 |
| 6,330,884 B1 | 12/2001 | Kim |
| 6,331,186 B1 | 12/2001 | Wang et al. |
| 6,334,871 B1 | 1/2002 | Dor et al. |
| 6,340,368 B1 | 1/2002 | Verbeck |
| 6,346,118 B1 | 2/2002 | Baker et al. |
| 6,355,060 B1 | 3/2002 | Lenker et al. |
| 6,358,556 B1 | 3/2002 | Ding et al. |
| 6,361,544 B1 | 3/2002 | Wilson et al. |
| 6,361,557 B1 | 3/2002 | Gittings et al. |
| 6,375,676 B1 | 4/2002 | Cox |
| 6,391,050 B1 | 5/2002 | Broome |
| 6,391,051 B2 | 5/2002 | Sullivan, III et al. |
| 6,395,017 B1 | 5/2002 | Dwyer et al. |
| 6,398,807 B1 | 6/2002 | Chouinard et al. |
| 6,402,777 B1 | 6/2002 | Globerman et al. |
| 6,409,750 B1 | 6/2002 | Hyodoh et al. |
| 6,409,752 B1 | 6/2002 | Boatman et al. |
| 6,409,755 B1 | 6/2002 | Vrba |
| 6,413,269 B1 | 7/2002 | Bui et al. |
| 6,416,542 B1 | 7/2002 | Marcade et al. |
| 6,428,566 B1 | 8/2002 | Holt |
| 6,436,134 B2 * | 8/2002 | Richter et al. ................. 623/1.15 |
| 6,440,165 B1 | 8/2002 | Richter et al. |
| 6,458,867 B1 | 10/2002 | Wang et al. |
| 6,464,721 B1 | 10/2002 | Marcade et al. |
| 6,471,721 B1 | 10/2002 | Dang |
| 6,475,208 B2 | 11/2002 | Mauch |
| 6,475,236 B1 | 11/2002 | Roubin et al. |
| 6,485,509 B2 * | 11/2002 | Killion et al. ................. 623/1.15 |
| 6,488,700 B2 | 12/2002 | Klumb et al. |
| 6,491,681 B1 | 12/2002 | Kunis et al. |
| 6,491,938 B2 | 12/2002 | Kunz et al. |
| 6,494,875 B1 | 12/2002 | Mauch |
| 6,497,916 B1 | 12/2002 | Taylor et al. |
| 6,503,271 B2 | 1/2003 | Duerig et al. |
| 6,508,836 B2 | 1/2003 | Wilson et al. |
| 6,514,281 B1 | 2/2003 | Blaeser et al. |
| 6,520,988 B1 | 2/2003 | Colombo et al. |
| 6,527,789 B1 | 3/2003 | Lau et al. |
| 6,533,810 B2 | 3/2003 | Hankh et al. |
| 6,562,063 B1 | 5/2003 | Euteneuer et al. |
| 6,579,314 B1 * | 6/2003 | Lombardi et al. ............. 623/1.44 |
| 6,592,615 B1 | 7/2003 | Marcade et al. |
| 6,596,020 B2 | 7/2003 | Vardi et al. |
| 6,596,023 B1 * | 7/2003 | Nunez et al. .................... 623/1.3 |
| 6,602,281 B1 * | 8/2003 | Klein ........................... 623/1.15 |
| 6,610,087 B1 | 8/2003 | Zarbatany et al. |
| 6,613,072 B2 | 9/2003 | Lau et al. |
| 6,613,075 B1 | 9/2003 | Healy et al. |
| 6,620,194 B2 | 9/2003 | Ding et al. |
| 6,648,913 B1 | 11/2003 | Yee et al. |
| 6,652,576 B1 * | 11/2003 | Stalker ........................ 623/1.18 |
| 6,652,579 B1 | 11/2003 | Cox et al. |
| 6,656,212 B2 | 12/2003 | Ravenscroft et al. |
| 6,660,030 B2 | 12/2003 | Shaolian et al. |
| 6,663,665 B2 | 12/2003 | Shaolian et al. |
| 6,666,883 B1 | 12/2003 | Séguin et al. |
| 6,669,719 B2 | 12/2003 | Wallace et al. |
| 6,689,159 B2 | 2/2004 | Lau et al. |
| 6,692,483 B2 | 2/2004 | Vardi et al. |
| 6,695,875 B2 | 2/2004 | Stelter |
| 6,699,274 B2 | 3/2004 | Stinson |
| 6,702,846 B2 | 3/2004 | Mikus et al. |
| 6,706,062 B2 | 3/2004 | Vardi et al. |
| 6,709,440 B2 | 3/2004 | Callol et al. |
| 6,733,523 B2 | 5/2004 | Shaolian |
| 6,749,628 B1 * | 6/2004 | Callol et al. .................. 623/1.15 |
| 6,780,174 B2 | 8/2004 | Mauch |
| 6,827,735 B2 | 12/2004 | Greenberg |
| 6,863,685 B2 | 3/2005 | Davila et al. |
| 6,896,699 B2 | 5/2005 | Wilson et al. |
| 6,964,681 B2 | 11/2005 | Murray, III |
| 7,125,419 B2 | 10/2006 | Séguin et al. |
| 7,160,318 B2 | 1/2007 | Greenberg et al. |
| 7,238,197 B2 | 7/2007 | Séguin et al. |
| 7,243,408 B2 | 7/2007 | Vietmeier |
| 7,344,556 B2 | 3/2008 | Séguin et al. |
| 7,686,845 B2 | 3/2010 | Séguin et al. |
| 2001/0004705 A1 | 6/2001 | Killion et al. |
| 2001/0010013 A1 * | 7/2001 | Cox et al. ..................... 623/1.15 |
| 2001/0012943 A1 | 8/2001 | Shaolian et al. |
| 2001/0016768 A1 * | 8/2001 | Wilson et al. ................. 623/1.11 |
| 2001/0025195 A1 | 9/2001 | Shaolian et al. |
| 2001/0037138 A1 | 11/2001 | Wilson et al. |
| 2001/0037142 A1 | 11/2001 | Stelter et al. |
| 2001/0044595 A1 | 11/2001 | Reydel et al. |
| 2001/0044622 A1 | 11/2001 | Vardi et al. |
| 2001/0044647 A1 * | 11/2001 | Pinchuk et al. ............... 623/1.13 |
| 2002/0016597 A1 | 2/2002 | Dwyer et al. |
| 2002/0032479 A1 * | 3/2002 | Hankh et al. ................. 623/1.16 |
| 2002/0035389 A1 | 3/2002 | Richter et al. |
| 2002/0058984 A1 | 5/2002 | Butaric et al. |
| 2002/0068968 A1 * | 6/2002 | Hupp .......................... 623/1.15 |
| 2002/0072790 A1 | 6/2002 | McGuckin, Jr. et al. |
| 2002/0107330 A1 | 8/2002 | Pinchuk et al. |
| 2002/0123791 A1 | 9/2002 | Harrison |
| 2002/0143386 A1 | 10/2002 | Davila et al. |
| 2002/0193873 A1 * | 12/2002 | Brucker et al. ............... 623/1.35 |
| 2002/0198587 A1 | 12/2002 | Greenberg et al. |
| 2003/0074056 A1 * | 4/2003 | Killion et al. ................. 623/1.16 |
| 2003/0093109 A1 | 5/2003 | Mauch |
| 2003/0114912 A1 | 6/2003 | Séguin et al. |
| 2003/0125791 A1 | 7/2003 | Séguin et al. |
| 2003/0125802 A1 | 7/2003 | Callol et al. |
| 2003/0130720 A1 | 7/2003 | DePalma et al. |
| 2003/0139796 A1 | 7/2003 | Séguin et al. |
| 2003/0139803 A1 | 7/2003 | Séguin et al. |
| 2003/0144724 A1 | 7/2003 | Murray, III |
| 2003/0149472 A1 * | 8/2003 | Pinchuk et al. ............... 623/1.13 |
| 2003/0163188 A1 | 8/2003 | Haverkost et al. |
| 2003/0181973 A1 | 9/2003 | Sahota |
| 2003/0187494 A1 | 10/2003 | Loaldi |
| 2003/0196717 A1 * | 10/2003 | Nunez et al. .................. 139/1 R |
| 2003/0236567 A1 * | 12/2003 | Elliot .......................... 623/1.13 |
| 2004/0006381 A1 | 1/2004 | Séguin et al. |
| 2004/0098114 A1 | 5/2004 | Wilson et al. |
| 2004/0102838 A1 | 5/2004 | Killion et al. |
| 2004/0236409 A1 | 11/2004 | Pelton et al. |
| 2005/0049680 A1 | 3/2005 | Fischell et al. |
| 2005/0096726 A1 | 5/2005 | Séguin et al. |
| 2006/0069421 A1 | 3/2006 | Murray, III |
| 2006/0100685 A1 | 5/2006 | Séguin et al. |
| 2006/0142849 A1 | 6/2006 | Killion et al. |
| 2006/0259136 A1 | 11/2006 | Nguyen et al. |
| 2007/0067011 A1 | 3/2007 | Krolik et al. |
| 2007/0100425 A1 | 5/2007 | Séguin et al. |
| 2008/0046064 A1 | 2/2008 | Séguin et al. |
| 2008/0046072 A1 | 2/2008 | Laborde et al. |
| 2008/0161903 A1 | 7/2008 | Séguin et al. |
| 2010/0256744 A1 | 10/2010 | Séguin et al. |

FOREIGN PATENT DOCUMENTS

| | | |
|---|---|---|
| EP | 0 421 729 B1 | 1/1996 |
| EP | 0 698 380 A1 | 2/1996 |
| EP | 0 775 470 A1 | 5/1997 |
| EP | 0 941 716 A2 | 9/1999 |
| FR | 2 722 678 B | 1/1996 |
| JP | 01-299550 A | 12/1989 |
| JP | 3-151983 A | 6/1991 |
| JP | H04-064367 A | 2/1992 |
| JP | 6-007454 A | 1/1994 |

(56) References Cited

FOREIGN PATENT DOCUMENTS

| | | |
|---|---|---|
| JP | 7-308331 A | 11/1995 |
| JP | 11-512635 A | 11/1999 |
| JP | 2001-245886 A | 3/2001 |
| WO | WO 93/13824 A1 | 7/1993 |
| WO | WO 94/12136 A1 | 6/1994 |
| WO | WO 95/21592 A1 | 8/1995 |
| WO | WO 95/32757 A1 | 12/1995 |
| WO | WO 96/14028 A1 | 5/1996 |
| WO | WO 96/29955 A1 | 10/1996 |
| WO | WO 96/34580 A1 | 11/1996 |
| WO | WO 96/37167 A1 | 11/1996 |
| WO | WO 97/07752 A1 | 3/1997 |
| WO | WO 97/12562 A1 | 4/1997 |
| WO | WO 97/46174 A1 | 12/1997 |
| WO | WO 98/36709 A1 | 8/1998 |
| WO | WO 99/15103 A1 | 4/1999 |
| WO | WO 99/37242 A1 | 7/1999 |
| WO | WO 99/49812 A2 | 10/1999 |
| WO | WO 00/44307 | 8/2000 |
| WO | WO 01/39697 A1 | 6/2001 |
| WO | WO 01/60284 A1 | 8/2001 |
| WO | WO 02/28316 A2 | 4/2002 |
| WO | WO 02/60520 A2 | 8/2002 |
| WO | WO 2004/017865 A1 | 3/2004 |
| WO | WO 2004/041126 A1 | 5/2004 |
| WO | WO 2004/043301 A1 | 5/2004 |
| WO | WO 2008/131266 A1 | 10/2008 |

OTHER PUBLICATIONS

Keeley et al., "Immediate and Long-Term Results of Elective and Emergent Percutaneous Interventions on 5 Protected and Unprotected Severely Narrowed Left Main Coronary Arteries", *JAAC* vol. 83, pp. 242-246 (1999).

Maehara et al., Intravascular Ultrasound Assessment of the Stenoses Location and Morphology in the Left Main Coronary Artery in Relation to Anatomic Left Main Length, JAAC vol. 88, Jul. 1, 2001; pp. 1-4, © 2001 by Excerpta Medica, Inc.

Marco, J. et al., "Current Approach for Stenting Bifurcation Lesions", Thierry Lefevre, Yves Louvard, Marie-Claude Morice, *The Paris Course on Revascularization* 2004; 129-54.

Nayak et al., "Left Main Coronary Artery Rotation Atherectomy and Stenting", *Southern Medical Journal*, vol. 93, No. 4, pp. 415-423 (Apr. 2000).

Park et al., "Stenting of Unprotected Left Main Coronary Artery Stenoses: Immediate and Late Outcomes", *JAAC* vol. 31, No. 1, pp. 37-42 (Jan. 1998).

Tan et al., "Long-Term Clinical Outcomes After Unprotected Left Main Trunk Percutaneous Revascularization 9 in 279 Patients", *Circulation*, vol. 104, pp. 1609-1614 (2001).

Yachia, Daniel, Editor; *Stenting the Urinary System*, © Isis Medical Media Ltd, Oxford; 1998.

\* cited by examiner

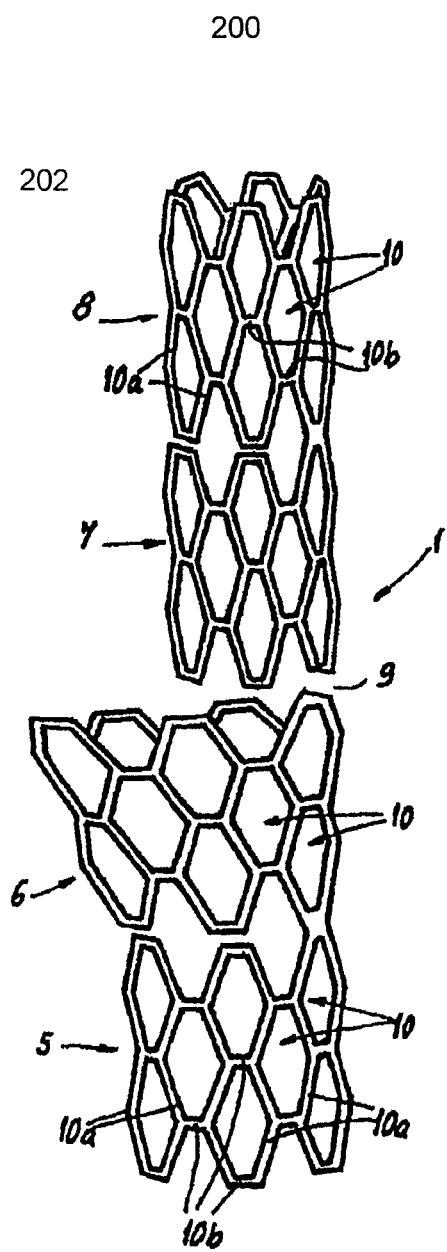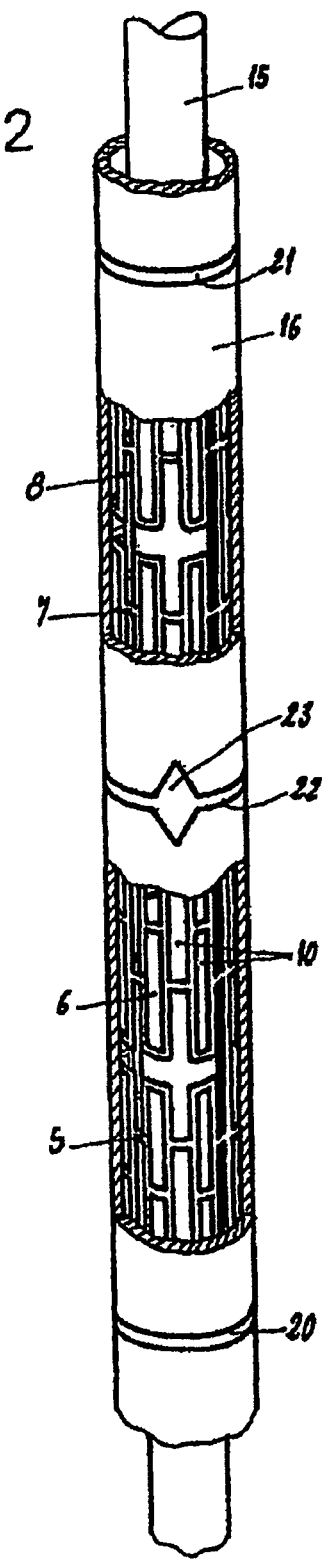

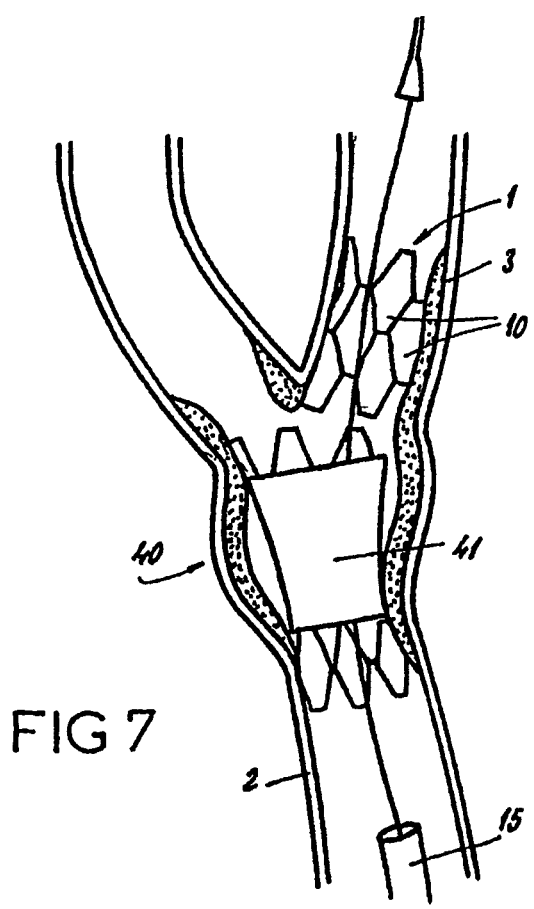
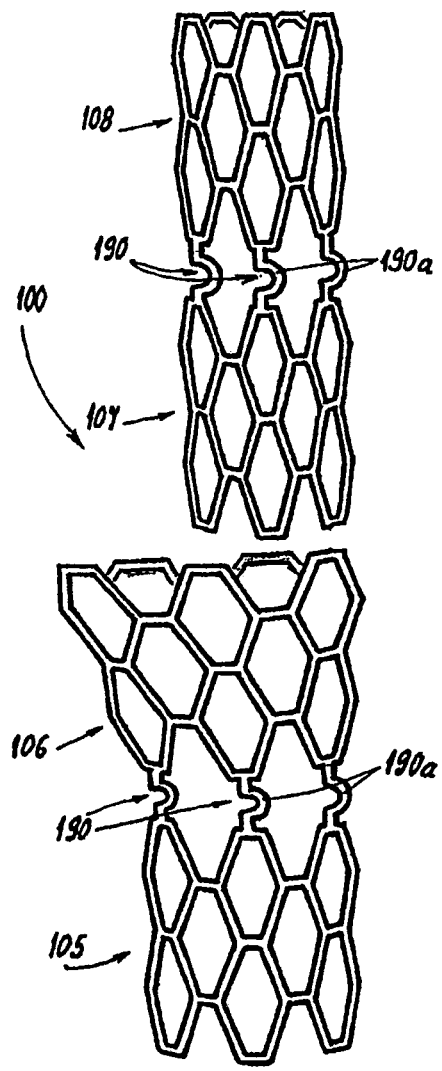

ENDOPROSTHESIS FOR VASCULAR BIFURCATION

CROSS-REFERENCES TO RELATED APPLICATIONS

This application is a continuation of U.S. patent application Ser. No. 11/124,905, filed May 9, 2005, now U.S. Pat. No. 8,231,667, which is a continuation of International Application No. PCT/EP02/12509, filed Nov. 8, 2002; the contents of each are herein incorporated by reference.

BACKGROUND OF THE INVENTION

The present invention relates to an apparatus and kit for the treatment of bodily conduits in the area of a bifurcation, that is to say in the area where a principal conduit separates into two secondary conduits. It also relates to equipment for positioning this apparatus.

The apparatus and kit of the invention can be used for the treatment of vascular bifurcations, in particular the carotid, femoral, iliac, popliteal, renal or coronary bifurcations, or nonvascular bifurcations, such as tracheal or biliary bifurcations, for example between the common bile and cystic ducts, or in the area of the bifurcation of the principal bile tract.

The treatment can consist in re-establishing the appropriate diameter of the bifurcation, in cases of arteriosclerosis or internal cell proliferation, in rectifying a localized or non-localized dissection in the wall of the conduit, or, in cases of aneurysm, in recreating a bifurcation of normal diameter, while eliminating the aneurysmal pouch.

DESCRIPTION OF THE PRIOR ART

It is known to treat narrowing of a rectilinear blood vessel by means of a radially expandable tubular apparatus, commonly referred to as a stent. This apparatus is introduced in the unexpanded state into the internal lumen of the vessel, in particular by the percutaneous route, as far as the area of narrowing. Once in place, it is expanded in such a way as to support the vessel wall and thus re-establish the appropriate cross section of the vessel.

The apparatus can be made of a non-elastic material, and in this case is expanded by means of an inflatable balloon on which it is engaged, or can be self-expanding, that is to say made of an elastic material, expanding spontaneously when withdrawn from a sheath which is holding it in the contracted state.

U.S. Pat. Nos. 4,733,665 and 4,886,062 are illustrative of existing apparatuses and of corresponding positioning techniques.

A conventional stent is not entirely suitable for the treatment of a narrowing situated in the area of a bifurcation, since its engagement both in the principal conduit and in one of the secondary conduits can cause immediate or delayed occlusion of the other secondary conduit.

It is known to reinforce a vascular bifurcation by means of a apparatus comprising two elements, each formed by helical winding of a metal filament. One of the two elements has two parts of diameter corresponding respectively to the diameter of the principal vessel and to the diameter of one of the secondary vessels, and is intended to be engaged on the one hand in this principal vessel and, on the other hand, in this secondary vessel. The other element has a diameter corresponding to the diameter of the other secondary vessel and is coupled to the first element, after the latter has been put into place, by engaging one or more of its turns in the turns of the first element.

This equipment permits reinforcement of the bifurcation but appears unsuitable for treating a vascular narrowing or an occlusive lesion, in view of its structure and of the low possibility of radial expansion of its two constituent elements.

Moreover, the shape of the first element does not correspond to the shape of a bifurcation, which has a widened transitional zone between the end of the principal vessel and the ends of the secondary vessels. Thus, this equipment does not make it possible to fully support this wall or to treat a dissection in the area of this wall. In addition, the separate positioning of these two elements seems relatively difficult.

U.S. Pat. No. 5,683,449 to Marcade (Marcade) discloses a bifurcated graft formed from a series of individual components that are intraluminally delivered apart from one another and then assembled to form a fully supported structure. The system includes a base member and one or more grafts connected thereto. Marcade's system requires overlapping connection of its components in order to achieve a fully supported structure and to lock the components to one another, thereby assuring a secure assembly and minimizing the possibility of leakage. Marcade discloses further that systems and methods that do not employ such an overlapping system are prone to acute and chronic failure whereby the graft could become displaced or collapsed.

U.S. Pat. No. 6,068,655 to Seguin et al. (the 655 patent) discloses a apparatus having a first segment that is conical in shape, at least one secondary segment, and a flexible link between segments. The flexible link enables the adjustment of segments relative to each other, but maintains them in connection with one another, limiting their independent positioning.

SUMMARY OF THE INVENTION

Prior art apparatuses are not sufficient for treating areas of vascular bifurcation because they require a connection, either direct or indirect, between multiple apparatus segments. This connection forces segments to be aligned relative to one another, as opposed to being aligned according to the shape and curvature of bifurcated vessels to be treated. This decreases the flexibility of the apparatus. In addition, segments connected so as to be directly adjacent or overlapping further decrease the flexibility of the apparatus. Such apparatuses are problematic, for example, for treating a bifurcated secondary conduit that has an axis perpendicular to the axis of the primary conduit.

The present invention aims to overcome various of these disadvantages by making available apparatus with which it is possible to treat a pathological condition in the area of a bifurcation, by fully supporting the vascular wall and by being relatively simple to position.

The apparatus to which the invention relates comprises a conical segment shaped to conform to the shape of the bifurcation in the area of a widened transitional zone. The conical segment is shaped to conform to the increasing cross section of the principal conduit at an area of and facing the vascular bifurcation.

In embodiments, the distal end of the stent may expand to a diameter that is at least about 105% of the diameter of the proximal end of the stent. In embodiments, the distal end of the stent may expand to a diameter that is at least about 110% of the diameter of the proximal end of the stent.

In embodiments, the apparatus comprises only a body (i.e., segment) which has, in a predetermined expanded state, a truncated shape, corresponding to the shape of the bifurcation in the area of the widened transitional zone which separates the principal conduit from the secondary conduits. In this way, only a single stent is required to treat a vascular bifurcation, thereby eliminating the need for the surgical insertion, positioning and coordination of multiple stent segments.

In embodiments, the apparatus comprises:
- at least one radially expandable segment which has, in a predetermined expanded state, a cross section substantially greater than the cross section of one of the secondary conduits; and
- a segment which has, in a predetermined expanded state, a truncated shape, corresponding to the shape of the bifurcation in the area of the widened transitional zone which separates the principal conduit from the secondary conduits.

In these embodiments, the segments do not overlap one another, and are not linked together and preferably include no means for being linked together. In this way, optimal positioning of stent segments can be achieved independently from one another. For the purposes of this application, an "unlinked segment" is defined as an independent segment that is neither directly nor indirectly connected to any other surgical apparatus, such as additional stents or segments, when the independent segment is in its predetermined, fully expanded state.

For the sake of simplification, the segment which has, in the expanded state, a cross section substantially greater than the cross section of one of the secondary conduits will be referred to hereinafter as the "secondary segment," while the segment which has, in the expanded state, a truncated shape will be referred to hereinafter as the "truncated segment."

In embodiments, the conical stent body may be packaged with a packaging element in a kit for treating an area of vascular bifurcation. In embodiments, the kit may include only the conical stent body and packaging element. Alternatively, the kit may further include at least one secondary stent body.

The secondary segment is intended to be introduced into the secondary conduit in the contracted state and to bear, in the expanded state, against the wall of this conduit. This expansion not only makes it possible to treat a narrowing or a dissection situated in the area of this conduit, but also to ensure perfect immobilization of the apparatus in the conduit.

In this position of the apparatus, the truncated segment bears against the wall of the conduit delimiting the widened transitional zone of the bifurcation, which it is able to support fully. A narrowing or a dissection occurring at this site can thus be treated by means of this apparatus, with uniform support of the vascular wall, and thus without risk of this wall being damaged.

The two non-overlapping, unlinked segments orient themselves suitably independently from each other upon their expansion.

In embodiments, at least the truncated segment is covered by a wall which gives it impermeability in a radial direction. This wall makes it possible to trap, between it and the wall of the conduit, particles which may originate from the lesion being treated, such as arteriosclerotic particles or cellular agglomerates, and thus to avoid the migration of these particles in the body.

Moreover, the apparatus can permit treatment of an aneurysm by guiding the liquid through the bifurcation and thereby preventing stressing of the wall forming the aneurysm.

The segments can be made from tubes of material of a different diameter, with the tube for the truncated segment having a larger diameter than the tube for the secondary segment. The tubes may be comprised of the same material. The use of tubes of different diameters results in the truncated segment having a larger radial force, especially at larger diameters.

Alternatively, the segments can be made from a single tube with different patterns of cuts to result in different shapes and sizes.

The apparatus can comprise several secondary segments, placed one after the other, to ensure supplementary support of the wall of the secondary conduit. To this same end, the apparatus can comprise, on that side of the truncated segment directed toward the principal conduit, at least one radially expandable segment having, in the expanded state, a cross section which is substantially greater than the cross section of the principal conduit.

According to embodiments of the invention, apparatus segments have a meshwork structure, the meshes being elongated in the longitudinal direction of the apparatus, and each one having a substantially hexagonal shape; the meshes of the truncated segment have a width which increases progressively in the longitudinal sense of the apparatus, in the direction of the end of this segment having the greatest cross section in the expanded state.

This increase in the width of the meshes is the result of an increase in the length of the edges of the meshes disposed longitudinally and/or an increase in the angle formed between two facing edges of the same mesh.

In addition, the truncated segment can have an axis not coincident with the longitudinal axis of the secondary segment, but oblique in relation to this axis, in order to be adapted optimally to the anatomy of the bifurcation which is to be treated.

The apparatus can be made of a metal with shape memory. This metal is preferably the nickel/titanium alloy known by the name NITINOL.

The equipment for positioning the apparatus comprises means for permitting the expansion of this apparatus when the latter is in place. These means can comprise a removable sheath in which the apparatus is placed in the contracted state, when this apparatus is made of an elastic material, or a support core comprising an inflatable balloon on which the apparatus is placed, when this apparatus is made of a non-elastic material.

In either case, this equipment comprises, according to the invention, means with which it is possible to identify, through the body of the patient, the longitudinal location of the truncated segment, so that the latter can be correctly positioned in the area of the widened zone of the bifurcation.

In the case where the expansion of this same segment is not uniform in relation to the axis of the apparatus, the equipment additionally comprises means with which it is possible to identify, through the body of the patient, the angular orientation of the apparatus in relation to the bifurcation, so that that part of this segment having the greatest expansion can be placed in a suitable manner in relation to the bifurcation.

BRIEF DESCRIPTION OF THE DRAWINGS

To ensure that it is fully understood, the invention is again described hereinbelow with reference to the attached diagrammatic drawings which show, by way of non-limiting example, embodiments of the apparatuses to which the invention relates.

FIG. 1 is a side view thereof, according to a first embodiment;

FIG. 2 is a perspective view of apparatuses of the invention in a state of radial contraction, and, in partial cutaway, of the equipment allowing it to be positioned;

FIG. 7 is a view, similar to FIG. 3, of a bifurcation presenting an aneurysm, in which apparatuses of the invention are placed, and FIG. 8 is a side view of apparatuses according to a second embodiment.

DESCRIPTION OF EMBODIMENTS

Figure 3:
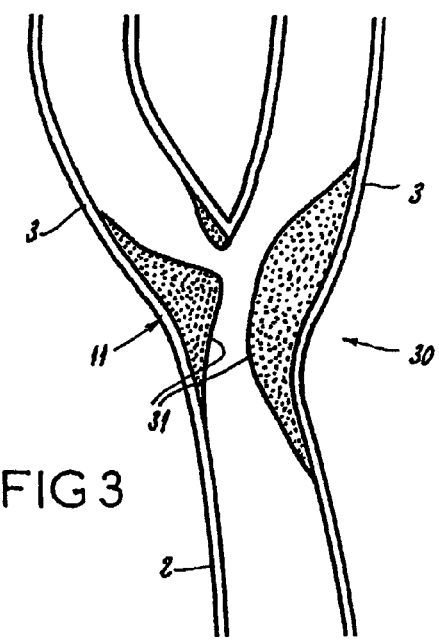
FIG. 3 is a longitudinal sectional view of a bifurcation to be treated.

FIG. 1 shows expandable apparatus 1 permitting the treatment of bodily conduits in the area of a bifurcation, that is to say, as is shown in FIG. 3, in the area where a principal conduit 2 separates into two secondary conduits 3.

In embodiments, the apparatus 1 comprises a conical segment having a proximal end 5 and a distal end 6, and at least one secondary segment(s) having a proximal end 7 and a distal end 8, each of meshwork structure, which are non-overlapping and unlinked as illustrated at 9. The apparatus 1 may optionally include a third segment 200, as well. In some embodiments, the third segment 200 has, in an expanded state, a substantially cylindrical shape and a cross section substantially greater than a cross section of a secondary conduit 3.

The meshes 10 of these segments are elongated in the longitudinal direction of the apparatus 1 and have in each case a substantially hexagonal shape.

The proximal end 5 of the conical segment has a tubular shape and has a diameter which is substantially greater than the diameter of the principal conduit 2.

The distal end 6 of the conical segment has meshes 10 whose width increases progressively, compared to that of the meshes of the proximal end 5, on the one hand in the longitudinal sense of the apparatus 1, in the direction of the end of the distal end 6 situated opposite the proximal end 5.

A transverse increase in the width of the meshes 10 may result from an increase in the length of the edges 10a of the meshes 10 disposed longitudinally, as well as an increase in the angle formed between two facing edges 10a.

This conical segment thus has a truncated shape with an axis which is oblique in relation to the longitudinal axis of the apparatus 1. This shape corresponds to the shape of the bifurcation in the area of the widened transitional zone 11 which separates the end of the principal conduit 2 from the ends of the secondary conduits 3.

In various alternate embodiments, the conical segment may continuously taper from the proximal end to the distal end, or the tapering may vary as appropriate.

The proximal end 7 and distal end 8 of the secondary segment have an identical diameter, which is substantially greater than the diameter of one of the secondary conduits 3.

The apparatus 1 may be made by appropriate cutting of a sheet of nickel/titanium alloy known by the name NITINOL, then folding the resulting blank into a circle and welding the parts of this blank which come into proximity with each other.

This alloy is malleable at a temperature of the order of 10° C. but can recover its neutral shape at a temperature substantially corresponding to that of the human body.

FIG. 2 shows the apparatus 1 in a state of radial contraction, obtained by cooling its constituent material. During this contraction, the edges 10a pivot in relation to the transverse edges 10b of the meshes 10, in such a way that the meshes 10 have, in this state of contraction, a substantially rectangular shape.

By virtue of this contraction, the segments 5 a cross section which is smaller than that of the conduits 2 and 3, and they can be introduced into these, as will be described hereinafter.

The apparatus 1 is engaged on a central support core 15, and is then contracted radially on the latter. This core 15 comprises an axial abutment such as a shoulder (not visible in FIG. 2) which has a diameter smaller than that of the apparatus 1 when this apparatus is expanded, but greater than the diameter of this apparatus 1 when the latter is contracted. This abutment consequently permits the axial immobilization of the apparatus 1 on the core 15 when the latter is contracted.

A sheath 16 is then engaged on the apparatus 1 in order to hold it in its contracted state. This sheath 16 may include, e.g., four radiopaque markers 20, 21, 22, 23 impressed on it, containing, for example, a barium compound. Three markers 20, 21, 22 have an annular 5 shape and extend round the whole periphery of the sheath 16. They are situated, respectively, in the area of the free ends of the segments. The fourth marker 23 is situated at substantially the halfway point of the generatrix of the segment 6. It has a diamond shape and a small thickness.

Figure 4:
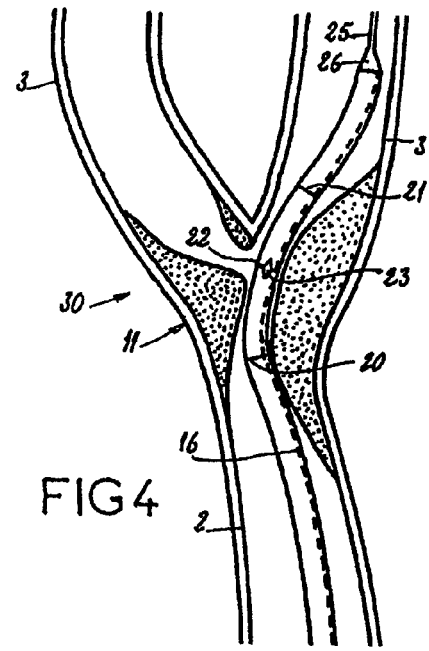
FIGS. 4 to 6 are views of this bifurcation similar to FIG. 3, during three successive stages of positioning of apparatuses of the invention.
Figure 5:
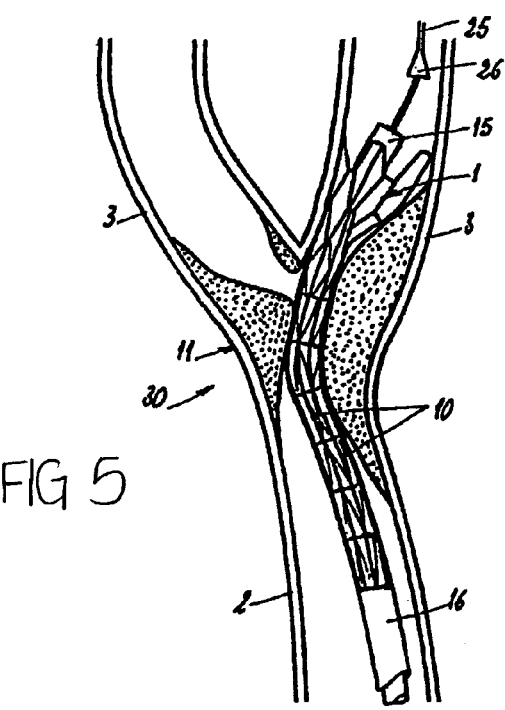
Figure 6:
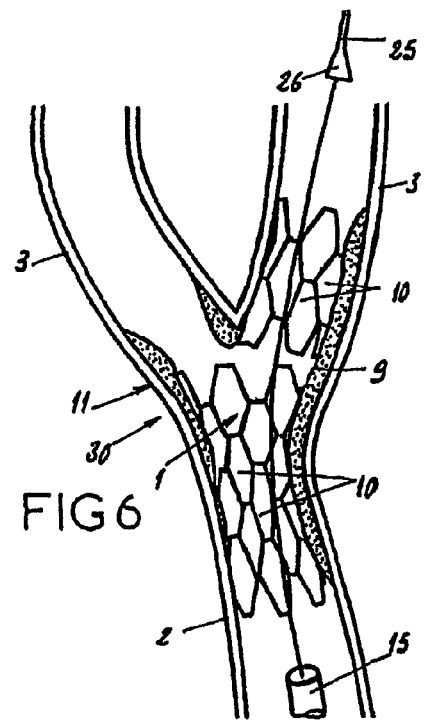

The core 15 has a longitudinal axial hole permitting its engagement on a guide wire 25 (FIGS. 4 to 6). This wire 25 can be engaged, by the percutaneous route, in the conduit 2, by way of the zone 11, and then in one of the conduits 3, through which it can slide, and comprises a cone 26 of synthetic material, situated in front of the assembly consisting of core 15, apparatus 1 and sheath 16.

The bifurcation 30 shown in FIG. 3 has excrescences 31 which create a narrowing in cross section, which impedes the flow of the liquid circulating in the conduits 2 and 3. In the case of a vascular bifurcation, these excrescences may be due, for example, to arteriosclerosis or cellular growth.

The apparatus 1 permits treatment of this bifurcation by re-establishing the appropriate diameter of the conduits 2, 3 and of the widened zone 11.

As appropriate, depending on whether reinforcement is needed in the secondary conduits, the conical segment may be used alone in the widened area of bifurcation, or it may be used in conjunction with one or more secondary segments.

In practice, as can be seen in FIG. 4, the assembly consisting of core 15, apparatus 1 and sheath 16 may be engaged on the wire 25 as far as the cone 26. By means of its sliding action, this wire 25 permits the engagement and then the guiding of this assembly in the conduit 2, the zone 11 and then the conduit 3. The cone 26 facilitates the sliding of the assembly and reduces the risk of trauma.

The marker 22 makes it possible to visualize, with the aid of a suitable radiography apparatus, the position of the conical segment, and thus to visualize the location of the conical segment so that it can be correctly positioned in relation to the widened zone 11.

With the markers 20 and 21 it is possible to ensure that the segments are correctly positioned in the principal conduit 2 and the secondary conduit 3.

The marker 23 is, for its part, visible in a plan view or an edge view, depending on whether it is oriented perpendicular or parallel to the radius of the radiography apparatus. It thus makes it possible to identify the angular orientation of the apparatus 1 in relation to the bifurcation 30, so that the part of the conical segment having the greatest expansion can be placed in an appropriate manner in relation to the zone 11.

The sheath 16, which has a length such that it opens out beyond the opening having permitted introduction of the assembly, is then progressively withdrawn, as is shown in FIGS. 5 and 6, in order to permit the complete expansion of the apparatus 1. The latter is reheated by the body temperature, and this permits its expansion, or it may expand by simple spring force without temperature effects. After complete expansion of the apparatus 1, the core 15 and the wire 25 are withdrawn.

FIG. 7 shows that the apparatus 1 can also be used to treat an aneurysm 40. At least a portion of the conical segment is covered by a polyester film 41, impermeable to the liquid circulating in the conduits, which film, for example, is sewn onto them. The apparatus then guides this liquid through the bifurcation 30 and consequently prevents stressing of the wall forming the aneurysm 40.

FIG. 8 shows an apparatus 100 according to the invention, having segments 105, 106, 107, 108, with a structure similar to that of the segments 5 to 8 in the apparatus shown in FIG. 1.

In the apparatus 100, individual segments include six omega-shaped bridges 190. The curved central part 190a of these bridges 190 has a multidirectional elasticity permitting the appropriate longitudinal orientation of the various segments in relation to one another.

The advantage of these bridges 190 is that they provide individual segments, and thus the apparatus, with longitudinal continuity, which facilitates the passage of said apparatus into a highly curved zone and which eliminates the need to reduce this curvature, which is always dangerous in the cases of arteriosclerosis, so as to permit the passage of the apparatus.

The invention thus provides apparatuses permitting the treatment of a pathological condition in the area of a bifurcation 30. These apparatuses have the many advantages indicated above, in particular those of ensuring a perfect support of the vessel wall and of being relatively simple to position.

It goes without saying that the invention is not limited to the embodiments described hereinabove by way of example, but instead embraces all the variant embodiments.

Thus, the apparatuses 1 and 100 can comprise a single, conical segment, or a conical segment and one or several secondary segments placed one after the other, in order to ensure supplementary support and, if need be, to increase the hold of the apparatus in the bifurcation 30.

The core 15 could comprise an inflatable balloon, either to effect the expansion of the apparatus 1, in the case where the latter is made of a nonelastic material, or to ensure the total expansion of a self-expanding apparatus 1 after the latter has been put into place.

The markers 20 to 23 could be impressed on the core 15 or directly on the apparatus 1.

The conical segment could have an axis coincident with the longitudinal axis of the apparatus, and not oblique in relation to this axis, if such is rendered necessary by the anatomy of the bifurcation which is to be treated.

In addition, the secondary segment could itself have, in the expanded state, a widened shape corresponding to the shape of the widened connecting zone via which, in certain bifurcations, the secondary conduits 3 are connected to the widened transition zone 11. The secondary segment would thus have a shape corresponding to the shape of this widened connecting zone, and would ensure perfect support thereof.

The bridges 190 could be greater or smaller in number than six, and they could have a shape other than an omega shape, permitting their multidirectional elasticity, and in particular a V shape or W shape.

As discussed above, the conical stent body may be packaged with a packaging element 202 in a kit for treating an area of vascular bifurcation. In embodiments, the kit may also include only the conical stent body and packaging element 202. Alternatively, the kit may further include at least one secondary stent body.

The stent system described may be adapted as mentioned above to treat any of a number of bifurcations within a human patient. For example, bifurcations of both the left and right coronary arteries, the bifurcation of the circumflex artery, the carotid, femoral, iliac, popliteal, renal or coronary bifurcations. Alternatively this apparatus may be used for nonvascular bifurcations, such as tracheal or biliary bifurcations, for example between the common bile and cystic ducts, or in the area of the bifurcation of the principal bile tract.

What is claimed is:

1. An assembly for positioning an apparatus for treating an area of bifurcation where a principal body conduit separates into at least two secondary conduits and wherein the principal conduit increases in cross section to the junction with the secondary conduits, said assembly comprising positioning equipment and the apparatus, the apparatus comprising a radially expandable first stent body configured to be engaged in the primary conduit in the area of bifurcation, wherein:
    said first stent body being radially expandable and having, in a predetermined fully expanded state, a first distal end having a greater diameter than a second proximal end, and a cross section substantially greater than a cross section of one of the secondary conduits;
    the first distal end being substantially conical and the second proximal end being substantially cylindrical;
    the first stent body being shaped to conform to the increasing cross section of the principal conduit, in the area of a widened transitional zone of the bifurcation that separates the principal conduit from the secondary conduits, in the direction of at least one secondary conduit, said first end opening out in the direction of said secondary conduits upon expansion;
    the first stent body being shaped to be independent of other stent bodies, and free of means for connecting to other stent bodies, when the first stent body is in a predetermined fully expanded state; and
    the positioning equipment being capable of carrying the stent.

2. The assembly of claim 1, further comprising at least one radially expandable second stent body having, in a predetermined fully expanded state, a substantially cylindrical shape, said second stent body being configured to be engaged in a said secondary conduit; the cross section of the at least one second stent body, in the predetermined fully expanded state, being less than the cross-section of the first distal and second proximal ends of the first stent body when the first stent body is in its predetermined expanded state.

3. The assembly of claim 2, said first and second stent bodies having a meshwork structure formed of meshes elongated in a longitudinal direction of the apparatus, each mesh having a substantially hexagonal shape, wherein the meshes of said first stent body have a width which increases progressively in the longitudinal direction of the apparatus with the meshes toward the first distal end of the first stent body having the greatest cross section in the expanded state.

4. The assembly of claim 2, the first stent body being configured to be engaged in the principal conduit only, and the at least one second stent body being configured to be engaged in one secondary conduit only.

5. The assembly of claim 2, said first and second stent bodies being made from first and second tubes of material, respectively, the first tube having a larger diameter than the second tube.

6. The assembly of claim 5, said tubes being made of the same material.

7. The assembly of claim 1, further comprising a plurality of radially expandable second stent bodies capable of being placed one after the other in a said secondary conduit and having, in the predetermined expanded state, a cross section that is substantially greater than the cross section of that secondary conduit.

8. The assembly of claim 1, wherein the first stent body is made from a single tube with different patterns of cuts.

9. The assembly of claim 1, wherein the first stent body is made from a nickel-titanium alloy.

10. The assembly of claim 1, wherein the positioning equipment comprises a support core and a retractable sheath.

11. The assembly of claim 10, wherein the support core is configured to support the first stent body in a contracted state.

12. The assembly of claim 10, further comprising markers on the sheath, the support core, and/or the first stent body.

13. The assembly of claim 10, wherein the support core comprises a longitudinal axial hole, such as a lumen, for engagement on a guide wire.

14. The assembly of claim 1, wherein the positioning equipment further comprises a marker to identify the angular orientation of the first stent body with respect to the bifurcation.

15. The assembly of claim 1, wherein the positioning equipment further comprises a marker to identify the longitudinal location of the first stent body with respect to the bifurcation.

16. A kit for treating an area of vascular bifurcation where a principal conduit separates into at least two secondary conduits and wherein the principal conduit increases in cross section to the junction with the multiple conduits, said kit comprising:

a packaging element, and the assembly of claim 1.

17. The kit of claim 16, said kit consisting only of said packaging element and the assembly of claim 1.

* * * * *